United States Patent [19]

Edgerton et al.

[11] 4,335,714
[45] Jun. 22, 1982

[54] IMPLANT FOR PENILE CONSTRUCTION

[75] Inventors: Milton T. Edgerton, Charlottesville, Va.; Roberto C. Granato, Elmhurst, N.Y.; Henry W. Lynch, Racine, Wis.

[73] Assignee: Medical Engineering Corporation, Racine, Wis.

[21] Appl. No.: 169,751

[22] Filed: Jul. 17, 1980

[51] Int. Cl.³ .............................................. A61F 5/00
[52] U.S. Cl. ..................................................... 128/79
[58] Field of Search .................. 128/79, 294, DIG. 9; D24/99

[56] References Cited

U.S. PATENT DOCUMENTS

| 837,993 | 12/1906 | Williams | 128/79 |
| 3,832,996 | 9/1974 | Kalnberz | 128/79 |
| 3,991,752 | 11/1976 | Gerow | 128/79 |
| 4,009,711 | 3/1977 | Uson | 128/79 |
| 4,066,073 | 1/1978 | Finney et al. | 128/79 |
| 4,204,530 | 5/1980 | Finney | 128/79 |
| 4,235,227 | 11/1980 | Yamanaka | 128/79 |

FOREIGN PATENT DOCUMENTS 2337206  6/1975  Fed. Rep. of Germany .

*Primary Examiner*—G. E. McNeill
*Attorney, Agent, or Firm*—Quarles & Brady

[57] ABSTRACT

An implant useful for the surgical construction of a penis comprises an elongated member having a pair of stems at the proximal end for anchoring the member in the pubic area of a patient, and a trunk with a urethra receiving and supporting groove and an open distal end. In the preferred embodiment, the implant is made completely of silicone elastomer. A method of constructing a penis using the implant is also described.

4 Claims, 7 Drawing Figures

IMPLANT FOR PENILE CONSTRUCTION

The present invention relates to a penile implant. More particularly, it relates to a penile implant which is useful in the surgical construction or reconstruction of a penis and to a surgical method of using the implant.

BACKGROUND OF THE INVENTION

Surgical efforts to perform transexual operations for patients desiring a sex change from female to male have been hindered by the surgeons inability to construct a satisfactory penis for the transexual patient due to the lack of a suitable implant which can be used as a supportive framework. For the same reason, efforts to surgically reconstruct a severely damaged penis have been less than completely successful. One surgeon has attempted to overcome the lack of availability of a suitable implantable supportive framework for these purposes by hand carving an implantable framework out of a block of silicone elastomer. Another surgeon's attempts to provide the framework have involved gluing together two composite penile rod implants of the type shown in U.S. Pat. No. 4,066,073 to form a unitary supportive framework. Still other surgeons have attempted to use as the supportive framework an inflatable penile implant of the type shown in U.S. Pat. No. 3,954,102. All of these attempts, although not completely successful, provide improved results as compared to the prior practice of constructing a penis entirely of skin without any supportive framework in which case the penis was only useful for urinary discharge.

SUMMARY OF THE PRESENT INVENTION

It is an object of the present invention to disclose a biocompatible penile implant which is particularly useful as a supportive framework for the surgical construction or reconstruction of a penis.

It is another object to disclose a penile implant which permits the construction or reconstruction of a penis which can be used for sexual intercourse.

It is a still further object to disclose a surgical method of constructing a penis employing the implant of the present invention.

The implant of the present invention is an elongated member of biocompatible material having a pair of stems at the proximal end for anchoring the member in the pubic area of a patient and to provide support for the penis, and a common intermediate trunk with a urethra receiving and supporting groove and an open distal end.

In the preferred method of the present invention, the implant is anchored by inserting each of the stems into a separate hole drilled in the pubic bone of the patient. The stems are retained in place by sutures tied to the stems and stitched to tendons. A urethra is made from a flap of the patient's skin by turning the skin side in and the raw side out and forming a tube. The thus formed urethra provides a smooth passage for urine. It is connected at one end to the urinary tract of the patient and the intermediate portion of the urethra is positioned in the urethra receiving and supporting groove in the trunk of the implant. The other or free end of the urethra is positioned in the open distal end of the implant. The implant with the urethra thus positioned in the groove is then covered with a second relatively thick flap of skin having the skin side out to form the penile shaft.

In the surgical reconstruction of a penis the implant is used as a framework in a similar manner, however, as much as possible of the original penile tissue is used.

The implant of the present invention makes it possible to provide the patient with a natural appearing penis which can be used for both urinary discharge end sexual intercourse.

These and other advantages and objects of the invention will be apparent to those skilled in the art from the description and drawing which follow:

DESCRIPTION OF THE PREFERRED EMBODIMENT

Figure 1:
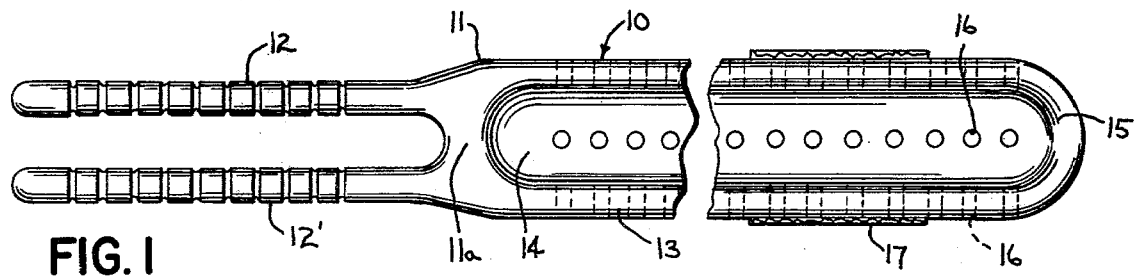
FIG. 1 is top plan view of one embodiment of the implant of the present invention.
Figure 2:
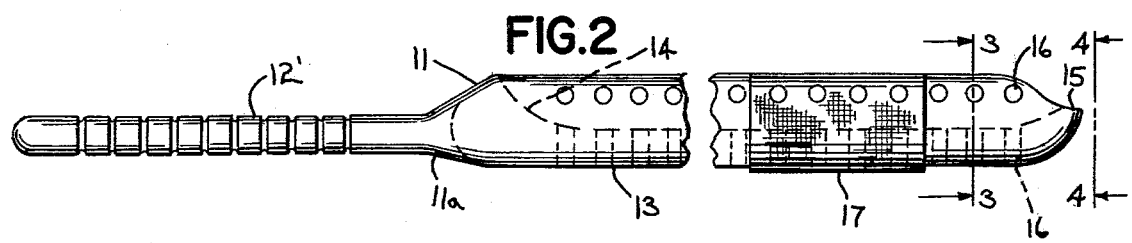
FIG. 2 is a side view of the implant of FIG. 1.
Figure 3:
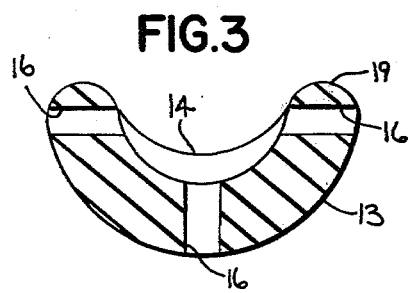
FIG. 3 is a sectional view taken along line 3—3 in FIG. 2.
Figure 4:
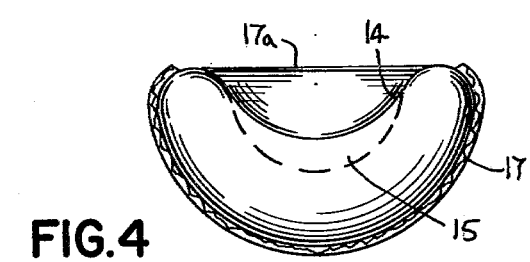
FIG. 4 is an end view of the implant taken along line 4—4 of FIG. 2.

As seen in FIGS. 1 to 4 of the drawing, the preferred embodiment of the implant of the present invention, which is generally referred to by the numeral 10, includes an elongated member 11 of biocompatible material having a pair of notched stems $12,12^1$ at the proximal end which are about 3 inches long, and an intermediate trunk 13 which is about 5 inches long and about ½ inch wide. The intermediate trunk has an open top with a urethra receiving and supporting groove 14 which extends from a point 11a adjacent the junction at which the stems $12,12^1$ join the trunk 13 to the open distal tip 15 at the other end of the member 11. The trunk 13 of the implant probably has a number of openings 16 extending completely therethrough to permit vascularization. The trunk 13 also may have secured thereto a number of porous patches 17 (only one of which is shown) for tissue ingrowth to assist in stabilizing the implant 10. The edges of the trunk 13 and the tip 15 are blunted or arced as at 19 to help prevent erosion of implant through tissue.

The entire implant 10 is preferably molded of medical grade silicone rubber which possesses suitable tensile strength and stiffness or hardness for its intended function. Other materials possessing the desired properties also may be used.

The stiffness or hardness of the material may be measured with a durometer, such as a Shore A durometer, which ascertains the depth of penetration of a specified indentor into a specimen under specified conditions. A scale is chosen so that zero represents a material showing no measurable resistance to indentation and 100 represents a material showing no measurable indentation.

Tensile strength is the unit stress which produces failure of a specimen in tension. A Scott Tensile Tester may be used for this purpose.

The entire implant is preferably molded of a material having a Shore A hardness of about 50 and a tensile strength of about 1000 psi. However, if desired, an implant made up of a composite of materials of different stiffness and strength can be prepared in the manner described in U.S. Pat. No. 4,066,073. The composite implant would be substantially identical in appearance to the embodiment of FIGS. 1 to 4 but would differ in that the stems 12,12¹ would be of a relatively stiff material, Shore A hardness 70; there would be a hinge section at 11a of more flexible material, Shore A hardness 20, and the trunk 13 would be of the relatively stiff material. The entire implant 10 could be covered by a layer of very soft silicone material, if desired. Such a composite implant would provide the advantages of providing stiffness to the penis when desired and enabling it to be conveniently and easily bent so as to be unobtrusive.

Figure 5:
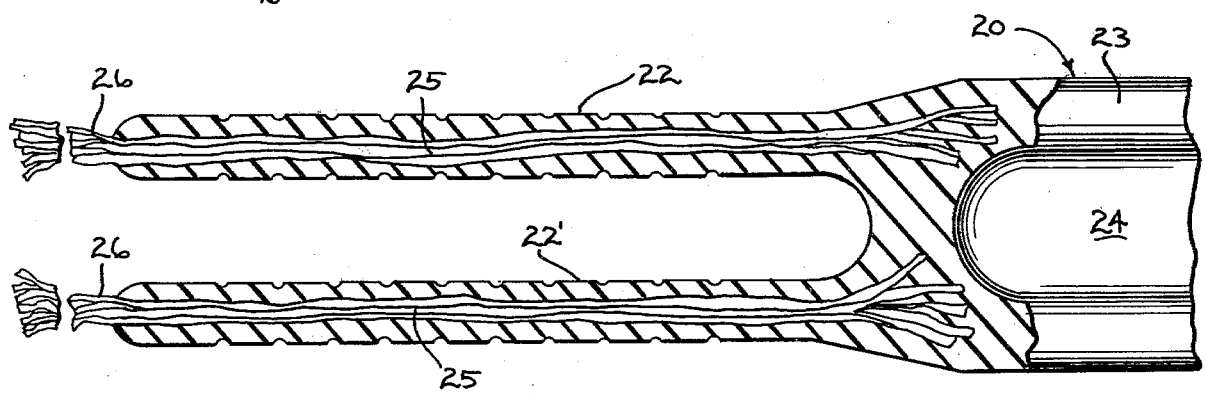
FIG. 5 is a partial sectional view of a second embodiment of the implant of the present invention.

Another embodiment of the invention is shown in FIG. 5. The penile implant 20 seen therein is an elongated member 21 having a pair of stems 22,22¹, a trunk 23 with a urethra receiving and supporting groove 24 and an open distal end (not shown). It differs from the previous embodiment primarily in that the stems 22, and 22¹ are reinforced by dacron threads 25 embedded in the material of the implant 20. The dacron threads 25 have free ends 26 which extend outwardly to provide integral means for stitching or tying the implant 20 in place.

The implants 10 or 20 are preferably compression molded of the desired biocompatible material. Reinforcing materials such as inserts of malleable metal, or of stiffer plastic can be molded into the implant if additional strength is desired. The openings 16 preferably are formed in the implant after is is removed from the mold by punching or drilling.

The porous patches 17 may be of any biocompatible material, such as polyester fabric, felt or an open foam. The patches preferably are affixed to the implant 10 or 20 by use of a suitable adhesive, which of course must also be biocompatible. It is to be understood that the implant need not have any patches at all if desired.

Figure 6:
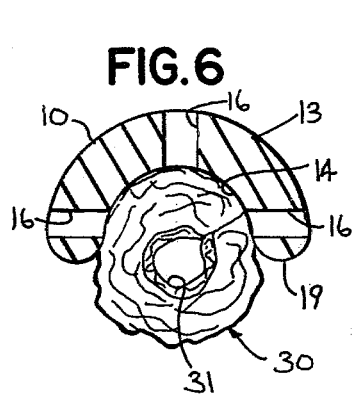
FIG. 6 is cross sectional view showing a urethra supported in an implant of the present invention.

The preferred method of using the implant 10 for the construction of a penis will now be described in connection with FIGS. 6 and 7.

After a suitable incision has been made to expose the pubic bone, a pair of holes are drilled, one on each side of the symphysis. Each of the stems 11,11¹ is drawn through a separate one of the holes and is attached posteriorly by stitching or tying to adjacent tissue. A urethra 30 is made by forming a tube about 5 inches long with the skin side 31 in from a relatively thin flap of the patient's skin, taken from the belly or thigh. The urethra 30 is attached at one end to the patient's urinary tract and the intermediate portion of the urethra is laid in the urethra receiving and supporting groove 14. The free end of the urethra 30 is trimmed, if needed, so that it terminates at the open distal tip 15. A second larger flap of the patient's skin, about ½ inch thick, with the raw side in, is used to form a cover 32 for the implant 10 and the urethra 30. The cover 32 is stitched to itself, the pubic skin of the patient and the urethra 30 to form the complete penis 33, which is about 5 inches long and 1½ inches in diameter. Conventional cosmetic surgery techniques are used to make the thus formed penis closely resemble a natural penis in appearance.

Figure 7:
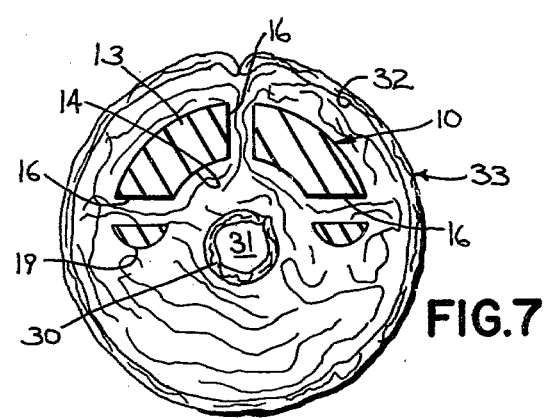
FIG. 7 is a cross sectional view of a penis in which the implant of the present invention serves as the supportive framework.

As can be seen in FIG. 7, the openings 16 in the trunk 13 permit vascularization to occur thus helping prevent necrosis of the thus formed penile tissue.

In a modification of the preferred method, instead of the drilling stem receiving holes in the pubic bone, the implant is anchored by sewing the stems to tissue along the rami.

In a reconstruction operation, the implant may be anchored in the described manner. However, not all the other described steps may be necessary depending upon the severity of the damage to the penis and the availability of the original penile tissue.

The implant 10 of the present invention may be molded in a single size which can be easily modified to fit the individual patient. In such an implant the stems 12,12¹ would be deliberately longer than is necessary thereby permitting them to be trimmed to the desired length at time of surgery.

It will be readily apparent to those skilled in the art that the embodiments shown in the drawing and the techniques described herein are only illustrative of the present invention and that a number of modifications and changes may be made without departing from the spirit and scope of the invention. For example, in addition to the stems being shortened at time of surgery it may also be desirable to modify the implant by trimming away material to permit the stems to diverge or converge to better fit the patient. Therefore, it is intended that the scope of the invention only be limited by the claims which follow.

We claim:

1. An implant for the construction or reconstruction of a penis, said implant consisting of a body member of biocompatible material having an elongated relatively rigid trunk with a urethra receiving groove extending longitudinally down the center thereof, one end of said trunk has a rounded tip and the other end of the trunk is connected by a flexible hinge to a pair of anchoring trimmable stems.

2. The implant of claim 1 in which the trunk is provided with means through which tissue can grow to provide vascularization of the urethra.

3. The implant of claim 1 which includes means for the ingrowth of tissue to anchor the implant.

4. The method of constructing a penis which comprises:
    (a) anchoring an implant of claim 1 in the pubic area of a patient by use of the stems;
    (b) making an urethra by forming a tube from the first flap of a patient's skin with the skin side in;
    (c) operatively connecting one end of the thus formed urethra to the urinary tract of the patient;
    (d) positioning the urethra in the urethra receiving groove of the trunk of the implant; and
    (e) covering the implant and the urethra with a second flap of relatively thicker skin with the raw side in to form a penis.

* * * * *